United States Patent
Yamada

(10) Patent No.: US 10,159,418 B2
(45) Date of Patent: Dec. 25, 2018

(54) INFORMATION OBTAINING APPARATUS, IMAGE CAPTURING APPARATUS, AND METHOD FOR OBTAINING INFORMATION

(71) Applicant: CANON KABUSHIKI KAISHA, Tokyo (JP)

(72) Inventor: Tomohiro Yamada, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 52 days.

(21) Appl. No.: 15/374,682

(22) Filed: Dec. 9, 2016

(65) Prior Publication Data
US 2017/0164844 A1    Jun. 15, 2017

(30) Foreign Application Priority Data

Dec. 11, 2015  (JP) .................................. 2015-242005

(51) Int. Cl.
  *A61B 5/00* (2006.01)
  *A61B 5/026* (2006.01)
  *G06T 7/00* (2017.01)

(52) U.S. Cl.
  CPC ........ *A61B 5/0261* (2013.01); *A61B 2576/00* (2013.01); *G06T 7/0012* (2013.01)

(58) Field of Classification Search
  CPC ... A61B 5/02007; A61B 6/5217; A61B 6/504; A61B 8/5223; A61B 5/02; A61B 5/026; A61B 5/0261; G06T 2207/30101; G06T 2207/30104
  See application file for complete search history.

(56) References Cited

U.S. PATENT DOCUMENTS

| | | | | |
|---|---|---|---|---|
| 2008/0269605 A1* | 10/2008 | Nakaya | ................ | A61B 5/6844 600/437 |
| 2011/0001761 A1* | 1/2011 | Sakuragi | ............ | A61B 5/02007 345/634 |
| 2011/0218427 A1* | 9/2011 | Kitamura | .............. | G06T 7/0016 600/425 |
| 2011/0237915 A1* | 9/2011 | Yamaguchi | ........ | A61B 1/00009 600/339 |
| 2013/0281852 A1* | 10/2013 | Mizukami | ............ | A61B 8/5223 600/438 |
| 2014/0031690 A1* | 1/2014 | Toji | .......................... | A61B 8/06 600/443 |
| 2014/0086459 A1* | 3/2014 | Pan | ..................... | G06K 9/00006 382/124 |
| 2014/0086461 A1* | 3/2014 | Yao | ........................ | A61B 6/032 382/128 |

(Continued)

FOREIGN PATENT DOCUMENTS

WO    2013/088566 A1    6/2013

*Primary Examiner* — Jingge Wu
(74) *Attorney, Agent, or Firm* — Canon U.S.A., Inc. IP Division

(57) ABSTRACT

An information obtaining apparatus capable of obtaining information about a blood vessel with high accuracy includes a first unit configured to obtain three or more image data pieces different in imaging conditions, a second unit configured to obtain a first index value of a first region and a second index value of a second region, a third unit configured to select a pair of the image data pieces from the three or more image data pieces using the first index value and the second index value of the image data, and a fourth unit configured to obtain information about a blood vessel using the selected pair of the image data pieces.

24 Claims, 11 Drawing Sheets

(56) References Cited

U.S. PATENT DOCUMENTS

| | | | | |
|---|---|---|---|---|
| 2014/0375631 A1* | 12/2014 | Masumoto | .............. | G06T 15/08 345/419 |
| 2015/0327780 A1* | 11/2015 | Kano | ................... | A61B 5/0261 600/407 |
| 2016/0029901 A1* | 2/2016 | Kuri | ................... | A61B 5/02007 600/301 |
| 2016/0302672 A1* | 10/2016 | Kuri | ........................ | A61B 8/04 |
| 2016/0310024 A1* | 10/2016 | Yoshida | ............... | A61B 5/0066 |

\* cited by examiner

INFORMATION OBTAINING APPARATUS, IMAGE CAPTURING APPARATUS, AND METHOD FOR OBTAINING INFORMATION

BACKGROUND

Field of the Disclosure

The present disclosure relates to an information obtaining apparatus, an image capturing apparatus, and a method for obtaining information.

Description of the Related Art

Apparatuses capable of capturing images of organizational structures, vascular structures, and others in living bodies include, for example, magnetic resonance imaging (MRI), and x-ray computed tomography (X-ray CT). However, these methods have issues in usage of contrast agents, radiation exposure, and the like, and thus observation methods are expected which prevent radiation exposure and are not invasive. There are measuring techniques using light as measuring methods which prevent radiation exposure and are not invasive.

However, living bodies are strong scatterers with respect to light, and in observation of tissues in the living bodies using light, scattered light causes blurring of organizational structures or lowering of image contrasts. Thus, in the observation of blood vessels such as thin blood vessels which easily cause lowering of contrasts due to scattering and new blood vessel groups which absorb less light and are low in contrasts, it is required to extract and emphasize blood vessel images.

International Publication No. WO 2013/088566 describes a technique for extracting a blood vessel pattern of a vein using a filter reducing frequency components lower and higher than a spatial frequency of the vein in a field of the vein authentication.

However, it is highly likely that an image of the new blood vessel group or the like has a low spatial frequency, and when the method according to International Publication No. WO 2013/088566 is used, it is difficult to extract a pattern of the new blood vessel group. Thus, a technique is required which can obtain information about a blood vessel with high accuracy regardless of a spatial frequency of a blood vessel image.

Accordingly, there is a need for an information obtaining apparatus that can obtain information about a blood vessel with high accuracy.

SUMMARY

According to an aspect of the present disclosure, an information obtaining apparatus includes a first unit configured to obtain three or more image data pieces different in imaging conditions, a second unit configured to obtain a first index value of a first region which is at least a part of a region corresponding to an artery, a vein, or a new blood vessel group and a second index value of a second region which is at least a part of a region other than the region corresponding to the artery, the vein, or the new blood vessel group in the image data, a third unit configured to select a pair of the image data pieces from the three or more image data pieces using the first index value and the second index value of the image data, and a fourth unit configured to obtain information about a blood vessel using the selected pair of the image data pieces.

According to another aspect of the present disclosure, a method for obtaining information includes obtaining three or more image data pieces different in imaging conditions, obtaining a first index value of a first region which is at least a part of a region corresponding to an artery, a vein, or a new blood vessel group and a second index value of a second region which is at least a part of a region other than the region corresponding to the artery, the vein, or the new blood vessel group in the image data, selecting a pair of the image data pieces from the three or more image data pieces using the first index value and the second index value of the image data, and obtaining information about a blood vessel using the selected pair of the image data pieces.

Further features of the present disclosure will become apparent from the following description of exemplary embodiments with reference to the attached drawings.

DESCRIPTION OF THE EMBODIMENTS

According to the present disclosure, a blood vessel part is a part including at least any one of an artery, a vein, and a new blood vessel group. A fat part is a part of a fat and a muscle, and the fat part does not include the artery, the vein, and the new blood vessel group, but may include a capillary.

Figure 1:
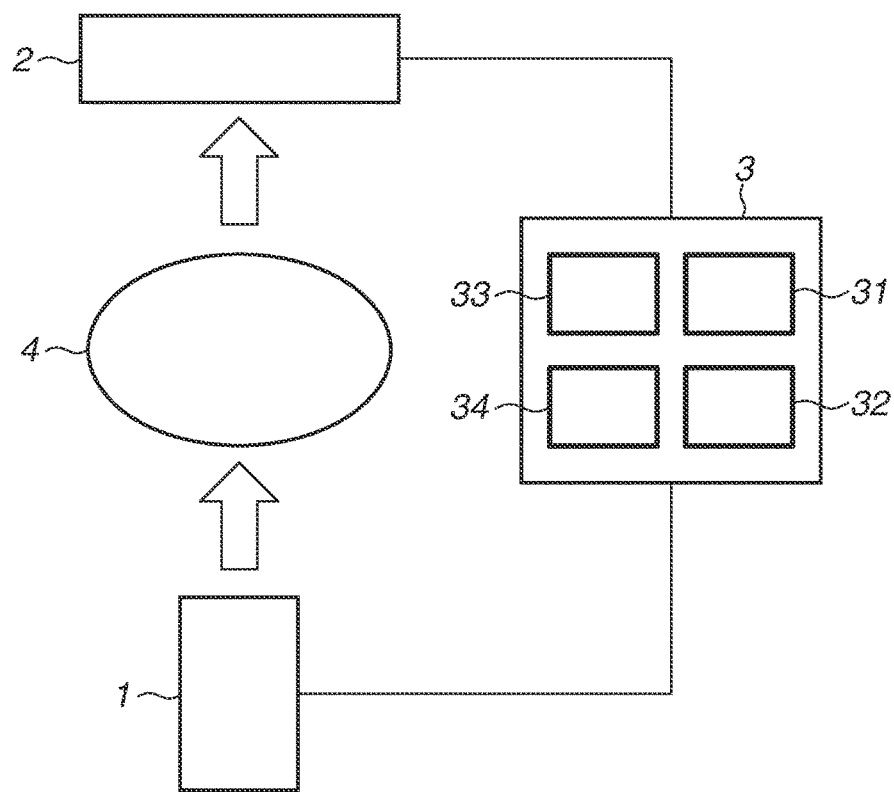
FIG. 1 is a schematic diagram illustrating an example of an image capturing apparatus according to one or more aspects of the present disclosure.

An image capturing apparatus according to one or more aspects of the present disclosure is described below. FIG. 1 is a schematic diagram illustrating an outline of the image capturing apparatus according to the present disclosure. The image capturing apparatus according to the present disclosure includes a light source 1, a detection unit 2, and an information obtaining apparatus 3. The light source 1 illuminates an imaging portion of a subject 4 including a blood vessel with light. The detection unit 2 detects the light emitted from the light source 1 and propagating through the subject 4 and generates an electrical signal. The light propagating through the subject 4 is at least one of the light transmitted through, reflected by, or scattered by the subject 4. In the case that the subject 4 is a living body, the living body is a strong scatterer, so that the light entering the living body is scattered, reflected, and adsorbed in the living body and partially comes out from the living body. The information obtaining apparatus 3 generates an image including at least a part of the subject 4 using the signal from the detection unit 2. The information obtaining apparatus 3 according to the present disclosure may be included in the image capturing apparatus or configured as an external apparatus different from the image capturing apparatus.

The information obtaining apparatus 3 includes a first unit 31 which obtains three or more image data pieces respectively having different imaging conditions. The information obtaining apparatus 3 includes a second unit 32 which obtains a first index value of a first region which is a part of a region corresponding to an artery, a vein, or a new blood vessel group and a second index value of a second region which is a part of a region other than the first region in the image data. The information obtaining apparatus 3 further includes a third unit 33 which selects a pair of the image data pieces from the three or more image data pieces using the first index value and the second index value of the image data and a fourth unit 34 which obtains information about a blood vessel using the selected pair of the image data pieces.

When a blood flow is varied in a human body, light absorption is varied in the blood vessel part. The present inventor found that a variation in a pixel value due to the variation in the blood flow can occur not only in the blood vessel part but also in the fat part. This is because, the fat part includes an extremely fine capillary, and thus blood and blood flow slightly exist therein. In addition, a diameter of the capillary is very thin compared to that of the artery and the vein, when a blood vessel is regarded as a flow channel, it can be considered that a pressure drop of the capillary is large. Therefore, as the blood vessel is thinner, it can be considered that a variation in a blood flow rate is smaller which is caused by a variation in a blood pressure due to an internal factor such as pulsation and an external factor such as a use of a tourniquet and the like. Thus, it can be considered that a behavior of a change in a pixel value due to the variation in the blood flow in the fat part is largely different from those in the artery and the vein.

According to the present disclosure, it is found that it is necessary to evaluate a change amount of pixel values between two images not only in the blood vessel part but also in the fat part so as to maximize a blood vessel image intensity of an image generated by differential processing. In other words, a change amount of a pixel value of the fat part near the blood vessel part is subtracted from a change amount of a pixel value of the blood vessel part in the two images, and the value thus obtained is evaluated to select a pair of images subjected to the differential processing. Accordingly, even from an image in which a blood vessel (absorption image) palely exists in a background distribution of scattered light, such as in normal transmission imaging, the blood vessel can be extracted by removing a scattered light component from the image by the differential processing between a plurality of images.

Various exemplary embodiments of the present disclosure will be described in detail below, however, the exemplary embodiments are not intended to limit the scope of the present disclosure. According to the exemplary embodiments described below, an example is described in which the information obtaining apparatus 3 is installed in the image capturing apparatus, however, the information obtaining apparatus 3 may be configured as an external apparatus different from the image capturing apparatus as described above.

FIG. 1 is also a schematic diagram illustrating an example of an image capturing apparatus according to a first exemplary embodiment. The image capturing apparatus includes the light source 1, the detection unit 2, and the information obtaining apparatus 3. It is desirable that the image capturing apparatus also includes a display unit (not illustrated) which displays a captured image and final images calculated by various arithmetic operations.

Figure 2:
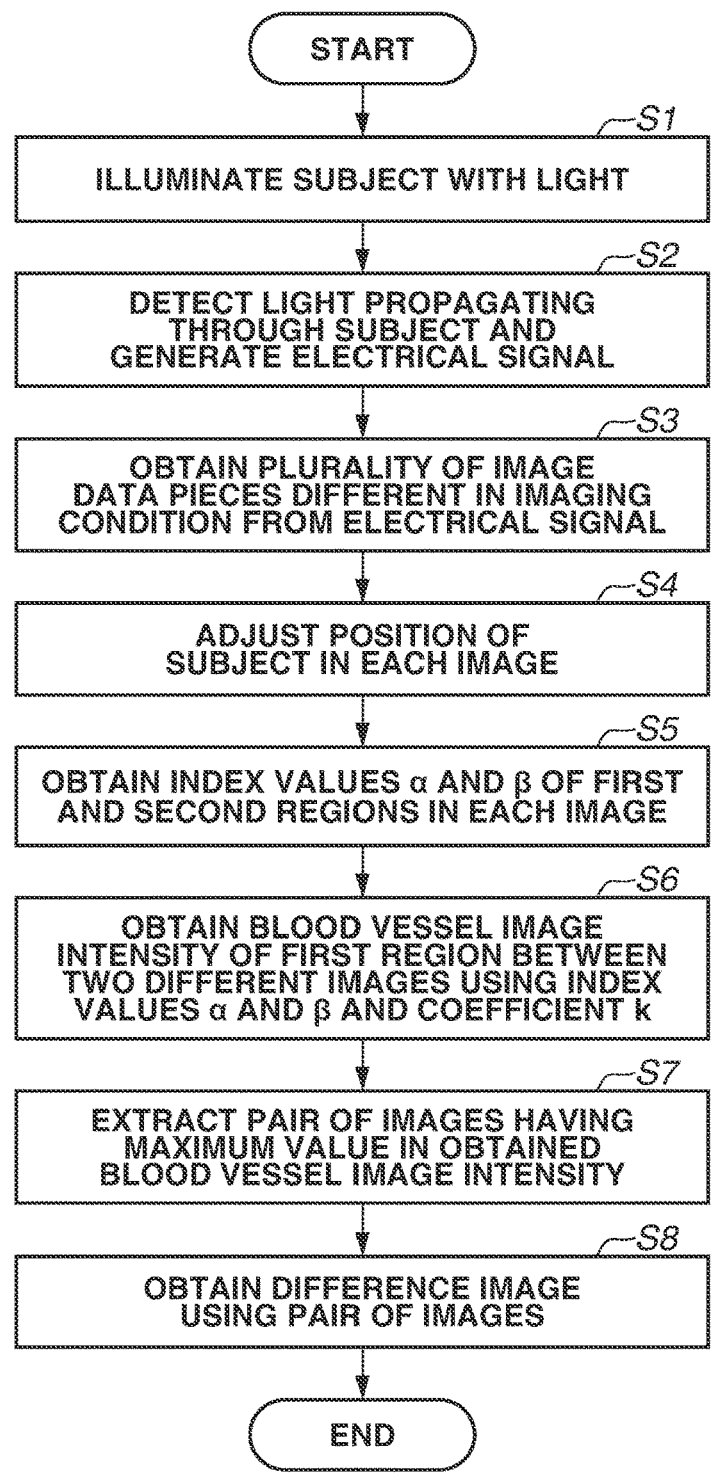
FIG. 2 is a flowchart illustrating an example of a method for obtaining information according to one or more aspects of the present disclosure.

An image forming method according to the present exemplary embodiment is illustrated in FIG. 2. According to the present exemplary embodiment, first, in step S1, the light source 1 illuminates the subject 4 with light. In step S2, the detection unit 2 detects the light propagating through the subject 4 and generates an electrical signal. Next, in step S3, the information obtaining apparatus 3 obtains a plurality of the image data pieces of which imaging conditions are different from the electrical signal generated in step S2. In step S4, the information obtaining apparatus 3 adjusts a position of a blood vessel part in each image.

Subsequently, in step S5, the information obtaining apparatus 3 obtains index values $\alpha$ and $\beta$ of first and second regions of each image. The first region is a region corresponding to the blood vessel part, and the second region is a region corresponding to the fat part. The first region and the second region may include one pixel or a pixel group including a plurality of pixels. When the first region and the second region each include one pixel, the index value is a pixel value. Whereas, when the first region and the second region are the pixel groups, an average value of pixel values of the plurality of pixels included in the pixel group, a maximum value or a minimum value in the pixel values of the plurality of pixels included in the pixel group, and the like can be used. The index value of the first region may be a value corresponding to the blood vessel part, and the index value of the second region may be a value corresponding to the fat part.

In step S6, a blood vessel image intensity of the first region between two different images is obtained using the index values $\alpha$ and $\beta$ and a coefficient k. The blood vessel image intensity is evaluated by a difference between a signal value of the blood vessel part and a signal value of a dark portion (the fat part) near the blood vessel. Specifically, the blood vessel image intensity is a difference between the index values of the first region and the index value of the second region.

In step S7, a pair of images is extracted in which the obtained the blood vessel image intensity has a maximum value. Lastly, in step S8, a difference image is obtained using the pair of images.

<Process for Illuminating with Light (Step S1)>

In the process, the light source 1 illuminates the subject 4 with light. The subject 4 is, for example, a finger of a person, especially a joint portion of the finger. In an articular rheumatism, a new blood vessel is formed in a joint portion. Thus, it is desirable that a region including a joint portion in a person's finger is illuminated with light as an imaging region.

As the light source 1, a light-emitting diode (LED) and a laser can be used. An irradiation wavelength from visible light to infrared light is desirable for imaging of a living body, and especially, near-infrared light having a wavelength of 1400 nm or less is desirable because of a high invasion depth to the living body. The light source 1 and the subject 4 may be separately arranged or arranged to be in contact with each other.

Further, it is desirable that the light source has a large area so as to be able to illuminate the imaging region as a whole to reduce an imaging time length, and the light source can be realized by forming as a plane light source, for example, arranging LEDs in an array. In addition, a configuration may be adopted which emits a thick parallel beam as illumination light. When an LED is used as the light source, the light source can be realized by collimating a single LED into an approximately parallel beam. When a laser is used as the light source, the light source can be realized by enlarging a light flux diameter to be parallel beam.

In addition, a configuration in which a diffusion plate is inserted between the light source and an observation portion is desirable since it can homogenize a light amount distribution of the light source, such as an LED array and illuminate an imaging subject with the light.

Further, when a laser is used as the light source, a configuration may be adopted in which the point light source is used as it is without enlarging the light flux diameter and imaging is performed while changing an illumination position using a scanning optical system of a galvano mirror and the like. Advantages of use of point illumination and the scanning optical system are that the illumination can be accurately performed to a desired illumination position, and the light amount distribution can be precisely realized using a sweeping speed or a stay time of the illumination position and light amount modulation of the light source itself. Further, it is desirable in that the light flux is small in diameter and easily interrupted, and thus light leakage and stray light can be easily suppressed.

Furthermore, it is desirable to scan a light receiving position synchronized with the scanning system of the light source since the scanning enables extraction of a component close to a straight-advancing component from light propagating through a scatterer, such as a living body. As the scanning system, a galvano mirror, a diaphragm and a slit which can perform position scanning at high speed, and the like may be used.

Further, in the case of an unpolarized light source, such as an LED, the light source can be configured as a polarized illumination by inserting a first polarizer between the light source and the observation portion. In this case, a second polarizer is inserted between the observation portion and a light receiver, so that a polarized component of the light transmitted through the observation portion can be detected.

In addition, a light source emitting light having a plurality of wavelengths may be formed by arranging LEDs having different emission wavelengths in an array. Alternatively, a light source of which an emission wavelength is changed with time may be used. When such a light source is used, a configuration may be adopted in which a wavelength is changed as a different imaging condition which is described below.

It is desirable that the subject 4 is held and fixed by a holding unit (not illustrated) such as a retainer. The retainer may have a function of holding an imaging portion of a subject person. The retainer may have a simple planer shape or a curved shape fitting to a shape of the imaging portion.

Further, for example, when the imaging portion is a hand, how to hold the imaging portion is different depending on whether to vertically or horizontally set an optical path of an imaging optical system, so that it is desirable that the retainer has an appropriate shape corresponding to the optical path of the imaging optical system.

In the case of a configuration in which the illumination light transmits through the retainer and the imaging portion, it is desirable that the retainer is constituted of a member having a high transmittance with respect to the illumination light. A configuration is also desirable in which a part of the retainer is constituted of a light-transmitting member or a transparent member, such as air, and a remaining part is constituted of a light shielding member so as to illuminate only a desired position of the observation portion with the illumination light.

Further, it is desirable that the retainer has a configuration which can change a holding height of the imaging portion according to a build, a height of a heart, and the like of a subject person. In addition, it is also desirable to have a function of changing the holding height for each image to be captured. By using such a configuration, a height relationship of the heart and the imaging portion is changed for each captured image, and a blood pressure of the imaging portion is correspondingly changed, and accordingly there is a possibility that captured images can be obtained each of which has a different blood flow rate and a different light absorption intensity by a blood vessel.

The retainer may have a configuration of which a temperature can be changed. When the temperature of the retainer is slightly warmer than a body temperature, the imaging portion of the subject person is warmed, and thus the blood flow rate of the imaging portion can be increased. Accordingly, there is a possibility that the blood vessel image is captured denser. In contrast, when the temperature of the retainer is lower than the body temperature, the temperature of the imaging portion is lowered, and there is a possibility that the blood flow rate of the imaging portion is reduced. As described above, when a function of changing the temperature of the retainer is provided, there is a possibility that captured images can be obtained each of which has a different blood flow rate and a different light absorption intensity by the blood vessel.

<Process for Detecting Light Propagating Through Subject and Generating Electrical Signal (Step S2)>

The detection unit 2 of the image capturing apparatus detects the light emitted from the light source 1 and propagating through the subject. Further, the detection unit 2 generates an electrical signal corresponding to an intensity of the light. The detection unit 2 may be separated from or in contact with the subject 4.

As the detection unit 2, a camera and a photodetector which are sensitive to an imaging wavelength are used. A camera which can obtain an image can be used as the detection unit 2. For example, in the case of a camera capable of outputting digital data, an output therefrom can be ultimately obtained as digital image data by a processing unit described below.

A blood vessel image in the living body becomes a pale image since the blood vessel is surrounded by scatterers, such as fat, a muscle, and a bone, and scattered light in the living body is superimposed therewith. Therefore, when the camera is used for imaging of the blood vessel in the living body, it is desirable that the camera has rich gradations and a function of certainly detecting distribution of a small light amount. It is also desirable that noise of the camera is small.

The camera may have a function of capturing a moving image in addition to a function of capturing a still image.

A photodetector may be used as the detection unit and combined with an optical system and an optical element for scanning a light receiving position to reconstruct an obtained image in a calculator from a light receiving position signal and an light amount signal. An electrical signal from the photodetector is an analog output. Thus, when the electrical signal is subjected to analog-to-digital (AD) conversion and taken into an arithmetic apparatus, such as a computer, it is desirable to perform the AD conversion having a high bit number. The photodetector is desirable since it includes a single element and is excellent in high speed and low noise properties.

<Process for Obtaining a Plurality of Image Data Pieces Different in Imaging Condition (Step S3)>

The information obtaining apparatus 3 generates an image in which the blood vessel is emphasized based on the electrical signal from the detection unit 2. The related processes are described below, and prior to that, the information obtaining apparatus 3 is described. The information obtaining apparatus 3 includes, for example, a computer. The information obtaining apparatus 3 may also include a capturing board for capturing the electrical signal from the detection unit 2 as necessary. The information obtaining apparatus 3 also has a program and an application installed therein which enable various arithmetic operations with respect to an image. Further, the information obtaining apparatus 3 may include a board and the like mounting the program as a circuit. At the same time, the information obtaining apparatus 3 may have a light source control function (monitoring and suppression of a variation in a light amount, adjustment of the light amount, selection of the wavelength, and the like).

The first unit 31 included in the information obtaining apparatus 3 obtains a plurality of the image data pieces different in imaging conditions. There is a method described below for obtaining the image data pieces by changing the imaging conditions. For example, a plurality of images can be captured by changing imaging time. Further, when a moving image is captured, each frame of the moving image can be regarded as a plurality of images captured by different imaging time. When a moving image is used, a temporal change of the blood vessel images can be recorded, and when the blood flow rate and the light absorption intensity by the blood vessel accompanying therewith are changed with time, the relevant change can be recorded.

The imaging condition to be changed is not limited to the imaging time but may be an irradiation wavelength of the light source and a wavelength of light to be detected. In order to obtain images by different irradiation wavelengths, for example, a light source having a wide band emission wavelength or a light source which can emit light in a plurality of wavelengths is used as the light source. Further, the optical path of the imaging optical system is divided, and the divided optical paths are combined with a configuration for introducing various optical elements, such as a wavelength selection filter. Alternatively, the optical path may be divided by wavelength using a wavelength separation element, such as a dichroic mirror. A plurality of optical sensors and cameras are used for each wavelength, and thus images can be captured in different wavelengths at the same time.

In the case of the configuration in which performs imaging by temporally changing the irradiation wavelength of the light source, the above-described element for dividing the optical path and the wavelength filter are not always necessary. The irradiation wavelength is changed with time, and imaging is performed in each case, so that captured images different in wavelength can be obtained. In addition, it is desirable to obtain various blood vessel images by appropriately combining the above-described different imaging conditions.

This process causes a difference in brightness of the blood vessel part among each of images. As the difference of the blood vessel image, there are, for example, a change in the transmittance and a change in the light absorption of the blood vessel part due to the variation in the blood flow rate. A factor or a method for causing the variation in the blood flow rate are as described below. For example, there is the variation in the blood flow always caused in the human body due to pulsation of the heart. In addition, when a positional relationship of a height of the imaging portion and a height of the heart of the subject person is changed, the blood flow can be varied. Alternatively, the blood flow in the imaging portion may be changed using a tourniquet (a cuff) and the like by changing a pressure for pressing a portion closer to the imaging portion than the heart.

Blood vessels normally existing in a human body are roughly classified into arteries, capillaries, and veins. When being further precisely defined, arteries are classified into main arteries, arteries, and arterioles. Inner diameters of a main artery, an artery, and an arteriole are respectively approximately 2.5 cm, 0.4 cm, and 30 µm. An inner diameter of a capillary is approximately 5 µm. When being further precisely defined, veins are classified into main veins, veins, and venules. Inner diameters of a main vein, a vein, and a venule are respectively approximately 3 cm, 0.5 cm, and 20 µm.

Generally, a liquid flowing in a tube receives a pressure drop. Thus, when a fluid flows in a tube under a certain pressure, the pressure is decreased as a diameter of the tube is thinner, and a distance propagating through the tube is longer. Therefore, it can be considered that, in the case of the blood vessel, a pressure from the heart or a pressure the blood returned to the heart and the variation thereof are easily propagated when the blood vessel is thicker and hardly propagated when the blood vessel is thinner. In other words, it can be considered that the pressure drop is small in the thick blood vessel, such as the artery and the vein, and the blood pressure from the heart and the variation thereof are easily propagated, so that a change in the blood flow rate due to the blood pressure variation is large. On the other hand, it can be considered that, the blood pressure and the variation thereof is hardly propagated in a very thin blood vessel, such as the capillary, and a change in the blood flow rate due to the blood pressure variation is small. When not only a thickness but also a structure of the blood vessel are different, it can be considered that a difference of elasticity of a blood vessel wall has an influence on ease of propagation of the blood pressure and the variation thereof. Therefore, it can be considered that a change in the light absorption of the blood vessel due to the blood pressure variation is also different depending on a type and thickness of the blood vessel.

It is not a blood vessel always existing in the human body, there is a new blood vessel which is a blood vessel newly generated in an affected part of a disease. Each one of new blood vessels is a thin blood vessel but forms a dense new blood vessel group by crowding together. In addition, a size as of a mass of the new blood vessel group and a thickness of each new blood vessel included in the new blood vessel group may be increased in some cases as the disease progresses. In a tissue in which the new blood vessel group is newly generated, the new blood vessel group is formed in addition to the capillaries and other blood vessels originally existing, and thus it can be considered that a volume share of the blood vessel and blood is increased. Thus, it can be considered that the light absorption by the blood and a change in the light absorption due to the variation in the blood flow rate will be increased compared to a tissue in which the new blood vessel group does not exist.

When a wavelength is changed as a different imaging condition, the blood vessel image can be captured using a light having a different wavelength. In this configuration, the blood vessel images of which intensities of absorption and scattering are different can be obtained by changing a wavelength of the illumination light through the use of wavelength dependencies of an absorption spectrum and a scattering spectrum of the blood vessel and a tissue around the blood vessel in the imaging portion. In this case, the above-described optical system which can perform illuminating and imaging in the different wavelengths is required, however, images different in imaging conditions can be obtained at the same time, so that an influence that a change in the blood vessel image due to a temporal change in a human body state is included as a difference between captured images can be reduced.

<Process for Adjusting Position of Blood Vessel Portion in a Plurality of Images (Step S4)>

The information obtaining apparatus 3 performs processing for adjusting a position of the subject in a plurality of images. This is because the imaging portion of the subject person sometimes moves during an imaging time. The imaging portion of the subject person is held by the retainer, however, breathing and other movements or an involuntary movement may occur in some cases. For example, in the case that a plurality of images is captured with a time interval, the imaging portion is highly likely to move with respect to the camera as the time interval is longer. Thus, it is necessary to obtain a correspondence relationship of the subject in the images for evaluation of the blood vessel intensity and generation of the difference images which are described below.

Any image can be used as an image to be a reference of the position adjustment, and an image captured at the beginning or the last may be used.

A method for adjusting positions of the blood vessel images in a plurality of images is not especially limited. For example, the blood vessel itself, a fingerprint, a wrinkle, a wound, and the like may be used as characteristic points in the image, and a parallel movement, a rotation, and a magnification between images can be adjusted using one or a plurality of these characteristic points.

The characteristic point is not limited to an innate characteristic point of the subject person as described above, and it is desirable to apply a marker to a part in the imaging portion of the subject person before imaging. It is desirable to apply a plurality of markers. In addition, it is desirable that the marker is applied three or more and at least three of these points are not on the same straight line.

<Process for Obtaining Part of Index Value of First Region and Part of Index Value of Second Region (Step S5)>

The second unit 32 in the information obtaining apparatus 3 obtains a part of the index value of the first region and a part of the index value of the second region in each image subjected to the position adjustment. As described above, the first region is a region corresponding to the artery, the vein, and the new blood vessel group, and the second region is a region corresponding to the fat part. A case is described below in which the first region and the second region respectively include one pixel, however, the first region and the second region may include a plurality of pixels. In that case, an average of pixel values of the plurality of pixels in the region may be regarded as the index value of the blood vessel or the fat part. Using the average is desirable because if the image includes noise, an influence of the noise can be mitigated. When a noise value is temporally or spatially generated in a random manner, an influence of the noise can be mitigated by averaging pixel values of neighboring pixels. In that case, a noise width is reduced to $N/(M)^{1/2}$ approximately in proportional to a square root of a pixel number M used in the averaging processing. The first region in each image corresponds to each other. In addition, the second region in each image corresponds to each other.

First, a method for setting the first region and the second region is described. The present disclosure is directed to clear extraction of a blood vessel image, especially a new blood vessel group. When a blood vessel near a joint is imaged to capture an image of a new blood vessel group associated with articular rheumatism, the imaging region is set so as to include the joint and an artery or a vein. When the new blood vessel group is the target, it is desirable to set the imaging region to include the new blood vessel group, however, there is a possibility that it is difficult to find a position of the new blood vessel group from an image obtained by the transmission imaging or the like which is difficult to view the new blood vessel group and simple. In this case, an operation for extracting the artery and the vein is performed first as described below. When visibility of the new blood vessel group is improved and the position thereof can be specified by the operation, an arithmetic operation for further improving the visibility of the new blood vessel group is performed, so that the new blood vessel group can be more clearly extracted. In other words, the first region is set to the artery and the vein.

The transmission imaging is described below as an example. The blood vessel absorbs light and is darkly captured in the normal transmission imaging. In reflection imaging, the blood vessel also absorbs the light and is darkly captured. Tissues such as the fat part, a bone, and a muscle strongly scatter the light, so that when the artery or the vein in the living body under the skin is captured by the transmission imaging, the image of the artery or the vein is captured as a dark and blurred rod-like image. The fat, the muscle, and the like other than the blood vessel weakly adsorb the light compared to the blood vessel and are captured more brightly than the blood vessel image by the scattered light in the living body. As an image display method, brightness and darkness are reversed, and a portion causing the light absorption by the blood vessel can be displayed brightly and a portion causing no absorption can be displayed darkly.

In the following description, an image, namely a bright/dark reversed image is used in which bright/dark information of an original image is reversed with respect to imaging of the artery or the vein, and an absorption portion by the blood vessel is brightly captured, whereas the fat part and the like are darkly captured. However, the following description is not intended to limit the contents of the present disclosure.

According to the present disclosure, the blood vessel image intensity is evaluated by a difference of signal values between a brightest part almost at the center of the blood vessel and a dark part near the blood vessel. A part of which a transmitted light amount is large is a shallow portion under the skin in which the artery or the vein does not exist but the fat, the muscle, and the like exist, namely the fat part.

In contrast, the blood vessel strongly adsorbs the light in the blood vessel part, and thus the transmitted light amount is less than that of the fat part. The blood vessel part is bright in the bright/dark reversed image. Therefore, a region having a largest pixel value near the fat part is basically the blood vessel part and set as the first region.

When a plurality of the blood vessels exists in the vicinity, as the second region for evaluating the index value of the fat part, it is desirable that a point having the largest transmitted light amount located between a certain blood vessel and another blood vessel nearest to the certain blood vessel is regarded as a position of the fat part. The position of the fat part corresponds to a position having a darkest pixel value in the bright/dark reversed image.

Figure 3:
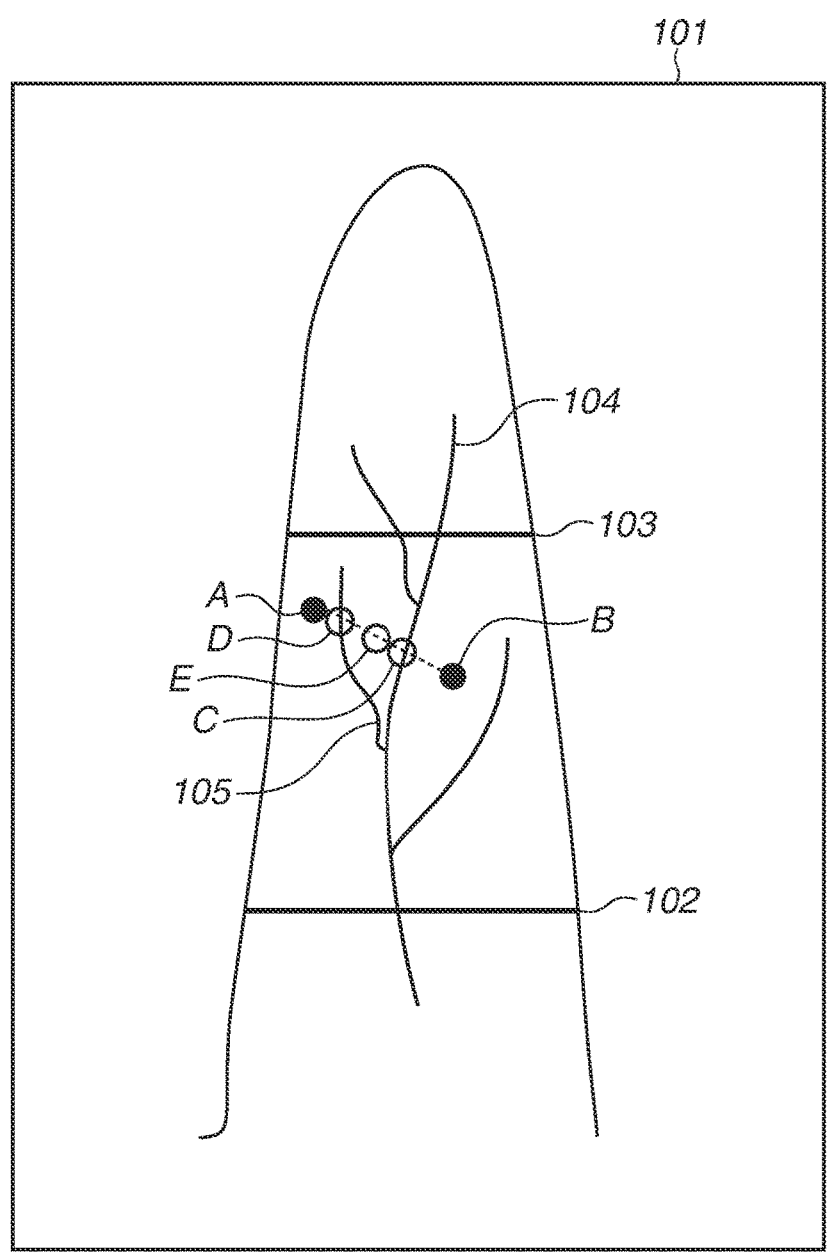
FIG. 3 illustrates a captured image for describing a first region and a second region.
Figure 4:
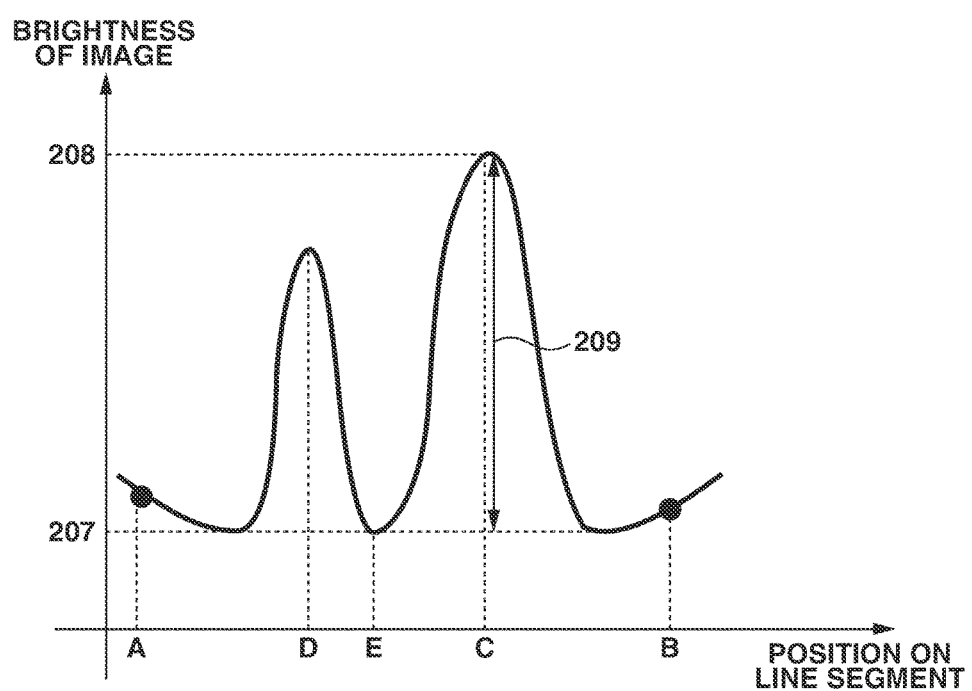
FIG. 4 illustrates index values and blood vessel image intensities of the first region and the second region in a single image according to one or more aspects of the present disclosure.

FIG. 3 illustrates image data generated by capturing an image of a person's finger. An imaging region 101 includes joints 102 and 103 and blood vessels 104 and 105 of the finger. FIG. 4 illustrates distribution of brightness of the image on a line segment connecting a point A and a point B in FIG. 3. Points C, D, and E located on the line segment AB in FIG. 3 are respectively a center of a blood vessel width of the blood vessel 104, a center of a blood vessel width of the blood vessel 105, and the fat part between the blood vessels 104 and 105. The points A to E in FIG. 3 respectively correspond to the points A to E in FIG. 4.

The point C is the blood vessel part, so that a pixel or a pixel group including the point C in the image data is set as the first region. The point D is also the blood vessel part, so that a pixel or a pixel group including the point D in the image data may be set as the first region. On the other hand, the point E is the fat part, so that a pixel or a pixel group including the point E in the image data is set as the second region. The pixel values are obtained from these regions as the index values of the respective regions. Further, in FIG. 4, a difference 209 between brightness 208 of the image at the point C (corresponding to the pixel value) and brightness 207 of the image at the point E (corresponding to the pixel value) is the blood vessel image intensity.

A user of the present apparatus may set the first region and the second region. In addition, the first region and the second region may be appropriately and automatically set using software by automatically determining where the artery, the vein, or the new blood vessel group exists in the image. For example, a technique for regarding a rod-like image as the artery or the vein, pattern matching using an image once captured the subject person, or the like can be used to recognize the blood vessel from the blood vessel image with respect to the images captured in the second time or later.

In the present description, an example is used in which a straight line connecting a position of the first region for evaluating the pixel value of the blood vessel image and a position of the second region for evaluating the pixel value of the fat part (the line segment AB in FIG. 3) is separated in an orthogonal direction with respect to a running direction of the blood vessel. However, the evaluation method of the blood vessel image is not limited to the above-described one, and the line may be shifted from the orthogonal direction.

It is desirable that the position of the first region and the position of the second region are set so as not to be largely separated from each other. For example, the first region and the second region are set so that another blood vessel does not intervene therebetween. Such setting facilitates evaluation of a difference of the pixel values between the blood vessel image and the nearest fat part, and thus it is desirable that an influence of background light intensity distribution by scattering is reduced, and the blood vessel image intensity can be easily evaluated with high accuracy. Further, it is because, if it is assumed that the blood vessel does not exist in the first region when the first region and the second region are close to each other, it can be considered that the pixel value of the first region is highly likely to close to the pixel value of the second region. The living body is a strong scatterer, and when the first region and the second region are sufficiently close to each other, it can be considered that the intensity distribution of the light transmitting through the living body scarcely includes spatial distribution by scattering. Therefore, it can be regarded that the difference of the pixel values between the first region and the second region is basically only influenced by presence or absence of the blood vessel, and the difference of the pixel values between the first region and the second region can be regarded as the blood vessel image intensity.

As the first region and the second region are separated from each other, a possibility increases that the intensity of the light transmitting through the living body is originally different in the first region and the second region regardless of presence or absence of the blood vessel. In this case, the blood vessel image intensity in the first region is deviated from the difference of the pixel values between the first region and the second region, and it becomes difficult to evaluate the blood vessel image intensity in the first region. Thus, it is desirable that the first region and the second region are not largely separated and set as near as possible in a state separated farther than a width of the blood vessel image.

In an image in which the blood vessel image is captured brightly and the fat part is captured darkly by reversing brightness and darkness of the blood vessel image, it is desirable to set the position of the second region as described below. It is desirable that the position to set the second region is on a straight line through the first region and extending in a direction orthogonal to the running direction of the blood vessel set in the first region and also a position located between the blood vessel set in the first region and the blood vessel next thereto at which the pixel value becomes a minimum value. When the brightness and darkness of the blood vessel image are not reversed, it is desirable to set a position at which the pixel value becomes the minimum value.

When a graph corresponding to that in FIG. 4 is generated from an actually captured image, noise is superimposed on the graph, and a minimum position of the pixel value, namely the position of the fat part is difficult to be found in the bright/dark reversed image in some cases. The noise is often a high spatial frequency component, and in that case, it is desirable that, for example, the noise is removed from the graph in FIG. 4 or original image data, a minimum position of the pixel value is found, and the second region is set to the relevant position to perform evaluation. As noise suppressing processing, for example, a low-pass filter, other various filters, moving average processing, and the like can be used. In addition, a noise width of the graph in FIG. 4 is separately evaluated, and the position of the fat part can be selected from any of pixels which have a pixel value (L+N) obtained by adding a noise width N to a minimum pixel value L between the blood vessel images. In this case, attention should be paid so as not to cause signal attenuation of a spatial frequency component corresponding to a size of a healthy blood vessel or the new blood vessel group as an observation target in the captured image.

In addition, when a region of interest (ROI) is set in the imaging region so as to include the above-described blood vessel image and a target portion thereof, and a lowest pixel value in the ROI is calculated, a contrast of the above-described blood vessel image in the ROI can be calculated.

An evaluation expression of contrast is, for example, as follows.

$$(I_{max} - I_{min})/(I_{max} + I_{min})$$

In the above expression, Imax is a pixel value of the brightest part at the center of the blood vessel image, and Imin is a pixel value of the fat part set aside of the blood vessel image. These pixel values are calculated in such a manner that a pixel value of a pixel having the lowest value in the ROI is regarded as zero (0), and the pixel values are calculated as differences therefrom. In a normal image in which brightness and darkness are not reversed, Imin is the pixel value of the darkest part at the center of the blood vessel image, and Imax is the pixel value of the fat part set aside of the blood vessel image. These pixel values are also calculated as differences from the pixel value having the lowest value in the ROI as described above. Alternatively, a different contrast definition expression may be appropriately used depending on an evaluation method of the blood vessel image.

Figure 5:
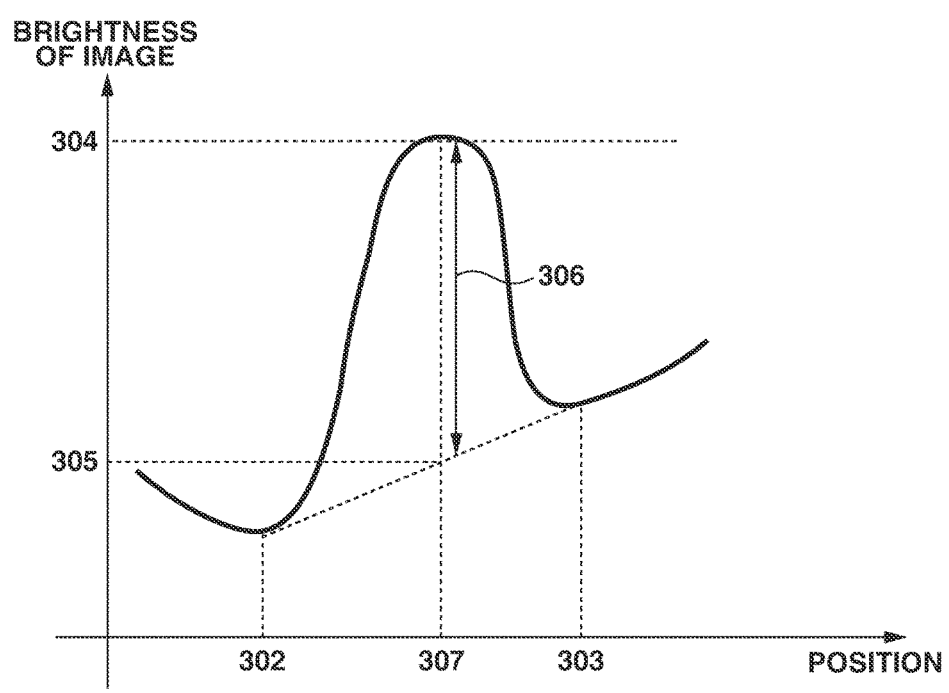
FIG. 5 illustrates index values and blood vessel image intensities of the first region and the second region in a single image according to one or more aspects of the present disclosure.

Regarding evaluation of the intensity of the above-described blood vessel image, brightness of the fat parts on both sides of the blood vessel image may be different according to an arrangement of the blood vessel and the observation portion of the subject person. For example, there is a case that distribution of pixel values including the blood vessel part is as illustrated in FIG. 5. The blood vessel image intensity in this case may be obtained in such a manner that, for example, a fat part having a larger pixel value or a smaller pixel value is selected from a fat part 302 and a fat part 303 on the both sides of the blood vessel part, and a difference of brightness between the selected fat part and a pixel value 304 at a center 307 of the blood vessel part is regarded as the blood vessel image intensity. Alternatively, a value 305 is obtained by dividing the pixel values the fat parts on the both sides of the blood vessel image at the center position of the blood vessel image, and a difference 306 of a height between the value 305 and the pixel value at the center of the blood vessel image may be regarded as the blood vessel image intensity. When intensities of a plurality of the blood vessel images are evaluated, it is desirable that a calculation method of the blood vessel image intensity is unified and applied to the plurality of the blood vessel images.

Depending on the subject person and the observation portion, positions of valleys of the pixel values corresponding to the fat parts on both sides of the blood vessel image are unclear in some cases. In such a case, it is desirable to calculate light scattering in advance based on a typical value of a scattering coefficient of a human body tissue by numerical calculation and the like and estimate how a blurred transmission image is indicated by the blood vessel image in a certain thickness and a certain depth. For example, a blur of a blood vessel image at a depth of 1 mm can be calculated from a half width at half maximum of a spatial extent of the light intensity distribution obtained by emitting a parallel beam from the point light source to one surface of a light scatterer corresponding to a human body tissue such as a fat layer of 1 mm thick and outputting from the other surface. Then, a pixel value of a portion separated from the center of the blood vessel image than the blur of the blood vessel image estimated as described above may be regarded as the pixel value of the fat part. For example, when the half width at half maximum of the blur of the blood vessel image is calculated as 2 mm, a point 2 mm or more away from the center of the blood vessel image is regarded as a pixel at the position of the fat part and set to the second region. The intensity of the blood vessel image can be evaluated from the pixel value of the fat part and the pixel value of the center of the blood vessel image thus estimated.

As described above, it can be considered that the artery, the vein, and the new blood vessel group existing near each other have similar modes of the temporal change in the respective blood flows. Thus, when a first image and a second image are selected in which a difference of the blood flows in the artery or the vein at a certain position is large, it can be estimated that a difference of the blood flows in the near new blood vessel group is also large. In other words, as a pair of optimum images for extracting the new blood vessel group in the vicinity of a certain joint, it is desirable that a part of the artery or a part of the vein in the vicinity of the joint is set to the first region.

However, in the case of the artery or the vein in the vicinity of the joint, a case can be considered in which the new blood vessel group exists very close thereto, or the new blood vessel group exists by overlapping in an optical axis direction of the imaging optical system. In such a case, there is a possibility that the new blood vessel group exists in a part regarded as the fat part aside of the artery or the vein when the intensity of the image of the artery or the vein is evaluated. In that case, there is a possibility that only a small change amount can be detected as an intensity change amount of the image of the artery or the vein in a plurality of images from which a change amount of the pixel value of the new blood vessel group is subtracted. Accordingly, it is likely to be difficult to select the pair of optimum images for extracting the blood vessel image.

Thus, when it is considered highly likely that a new blood vessel group exists in a certain joint, it is desirable to set a part of the artery or a part of the vein not in the vicinity of the joint is set to the first region so as to select and evaluate an optimum image for extracting an image of the new blood vessel.

<Process for Obtaining Blood Vessel Image Intensity of First Region Between Two Different Images (Step S6)>

Figure 6:
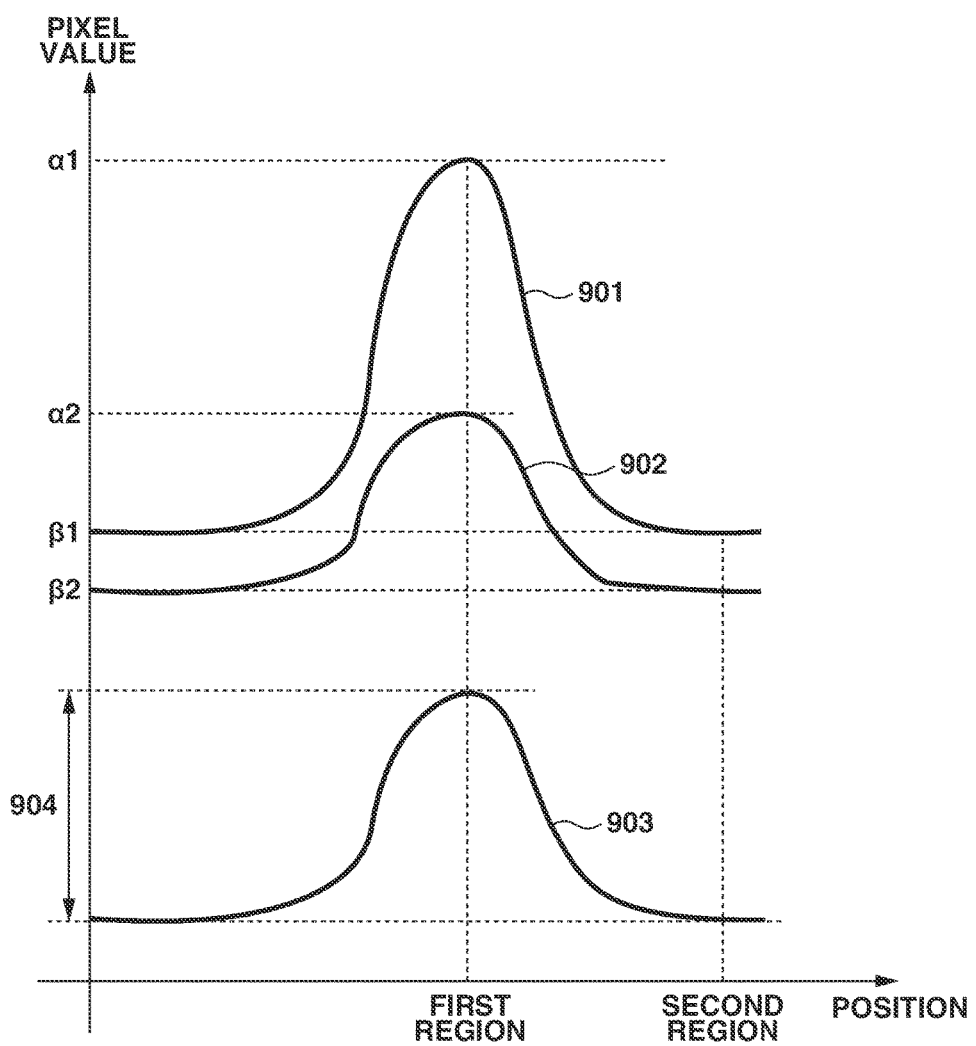
FIG. 6 illustrates index values and blood vessel image intensities of the first region and the second region in a difference image according to one or more aspects of the present disclosure.

The information obtaining apparatus 3 obtains the blood vessel image intensity of the first region between two different images. FIG. 6 illustrates pixel values of the first regions and the second regions of respective first image 901 and second image 902. Specifically, the pixel value of the first region and the pixel value of the second region in the first image 901 are respectively $\alpha 1$ and $\beta 1$. Further, the pixel value of the first region and the pixel value of the second region in the second image 902 are respectively $\alpha 2$ and $\beta 2$. A blood vessel image intensity 904 in the first region when a difference image 903 is generated by the differential processing of the first image 901 and the second image 902 is expressed by the following Expression 1. A coefficient k is a positive constant. Symbols | | means an absolute value.

$$|(\alpha 1 - k \cdot \alpha 2) - (\beta 1 - k \cdot \beta 2)| \qquad \text{Expression 1}$$

When the differential processing is performed on two images, the differential processing is performed by multiplying one of the images by a coefficient in the difference between the images. The coefficient k is a parameter, and a plurality of values of Expression 1 is calculated with respect to the coefficient k by substituting a value in a predetermined range in Expression 1. However, it is desirable to set the coefficient to one to simplify the arithmetic operation and enable high speed processing. The coefficient can be set to a constant other than one. For example, the coefficient is set so that the pixel value of the second region matches with each other in the two images. In other words, it is desirable that when it is set as $k = \beta 1 / \beta 2$, the brightness of the fat part can be approximately zero in the differential processing, and the blood vessel image intensity can be clarified.

As described above, the blood vessel intensity of the set first region is obtained with respect to all combinations of images and the coefficient k.

The differential processing is not limited to processing performed between single images. For example, an image A obtained by averaging ten images subjected to the position adjustment of the blood vessel part is prepared, and an image B obtained by averaging other ten images is also prepared to suppress random noise included in images. It is desirable to perform the differential processing of the image A and the image B. The number of images subjected to the averaging processing is not limited to ten images. It is necessary to increase a cumulative number of images to correspond to a desired noise reduction effect. The random noise is suppressed in proportion to a square root of the cumulative number, and it is necessary to generate an average image of 100 images so as to suppress the noise, for example, to $1/10$. The number of images subjected to the averaging processing can be set by a user of the apparatus while viewing the difference image or by the information obtaining apparatus 3 in such a manner that a signal to noise (SN) ratio is evaluated by setting the intensity of the blood vessel image as a signal value and a noise value as the random noise, and the number of images is set so that the SN ratio becomes a predetermined value or larger.

<Process for Extracting Pair of Images Having Maximum Value of Blood Vessel Image Intensity (Step S7)>

When there are hundreds to thousands of images obtained by capturing the same affected part in different conditions, it is very difficult for a parson to select two images optimum for generating a difference image from among these images, it is expected that the arithmetic operation unit automatically selects the optimum image. Therefore, it is desirable that an image optimum for generating the difference image is selected by a certain determination method.

Thus, the third unit 33 in the information obtaining apparatus 3 extracts a pair of images which maximize a value of Expression 1. When a difference image is generated using the pair of images, the blood vessel image intensity of the first region can be maximized in the difference images generated from the obtained images. Thus, the pair of images can be obtained by comparing Expression 1 with respect to the combinations of the images in step S6.

When a certain pixel value is focused, noise, such as camera noise and electrical noise, of which a value varies in each captured frame is superimposed on an image in some cases. Therefore, when a frame for maximizing Expression 1 is selected, it is desirable to consider that the noise is superimposed on each pixel value. For example, it is assumed that Expression 1 has a value V when the first image and the second image for maximizing the value of Expression 1 is selected. In addition, noise superimposed on each pixel value is separately evaluated, and the value is assumed as N. At that time, it can be considered that the value V includes an error about ±N caused by the noise, so that, in the case that the maximum value of Expression 1 is calculated as V, when Expression 1 actually has a value V−N or larger, the value can be regarded as the approximately maximum value.

Therefore, in the selection of the first image and the second image for maximizing Expression 1, the first image and the second image for making the value of Expression 1 (V−N) or larger can be selected. In this regard, when there is a plurality of candidates of the first image or the second image, any of these images may be selected as the first image and the second image, or images may be separately generated by performing the averaging processing and the like on these images. As the evaluation method of a noise value N included in a certain image, for example, when a moving image is captured in the same wavelength, the noise value can be read from a variation of a pixel value in a specific image for each frame.

The above-described differential processing of images may not be the differential processing between single images, and each image may be, for example, an average image of a plurality of images. In this case, it is desirable to use, for example, previous and subsequent frames including a frame extracted as optimum for the differential processing between the single images for selecting images subjected to the averaging processing. For example, frames including the optimum frame and temporally earlier or later than the optimum frame may be selected. Further, frames in previous and subsequent time slots including the optimum frame may be selected.

When a moving image is captured in a speed about a few to tens of fps, the frame rate is a sufficient high rate compared to the blood pressure variation and the pulsation in the human body. Thus, a high-speed pixel value variation superimposed on a certain pixel value for each frame can be regarded as noise. Standard deviation and a deflection width of the pixel value variation are evaluated, and the noise value can be calculated. Alternatively, for example, when dark noise, optical shot noise, and other specific noise are the main factors of the noise signal, these noise values are separately measured and used as the noise value.

Further, the first image and the second image for maximizing the value of Expression 1 may be selected by measuring a variation in the pixel value of the first region and the pixel value of the second region for each frame, removing a temporal high-frequency component by performing the low-pass processing and the like, and evaluating a low-frequency component.

A structure of the new blood vessel group is different from that of the blood vessels, such as the artery, the vein, and the capillary, always existing in the human body. Therefore, when a pressure is applied to the new blood vessel group similarly to these blood vessels, a magnitude and a speed of the variation in the blood flow caused at that time are likely to be different. For example, a case can be considered in which the variation in the blood flow of the new blood vessel group is caused slightly later than the variation in the blood flow of the artery and the vein, and the variation in the blood flow of the vein is caused further later than that. Further, it can be considered that the speed of the variation in the blood flow is faster in the thick blood vessels, such as the artery and the vein and is slow in the thin blood vessel, such as the new blood vessel group. Even the artery, the vein, and the new blood vessel group apparently exist near each other, it is highly likely that respective distances from the heart or a blood flow change unit, such as a cuff, are different. Thus, it is possible in some cases that the blood flow change is caused rather earlier in the new blood vessel group. However, in view of the structure in which the blood is supplied from the artery to the new blood vessel group and flows into the vein, it is unlikely that the time when the variation in the blood flow is caused in the new blood vessel group existing near the artery and the vein is largely different therefrom.

Therefore, when many of the blood vessel images are temporally obtained by capturing of a moving image and the like, it is desirable, in the view of shortening of time, that the artery or the vein is extracted by the differential processing, and a search for a pair of frames optimum for extraction of the new blood vessel group is started from previous and subsequent frames near a pair of frames with which the extracted artery or vein is easiest to be viewed.

Further, it is desirable that obtained images are sequentially processed in association with the progress of the imaging operation and obtainment of the image data pieces, and the imaging is terminated when a value evaluated according to the above-described Expression 1 reaches a certain value or more with respect to a plurality of images selected from the obtained images. In addition, it is desirable to have a function of notifying the termination of the imaging. There is a possibility that the function can finish the imaging of the subject person in a necessary minimum imaging time length and avoid an increase of a load on a user or the subject person of the present apparatus.

<Process for Obtaining Difference Image (Step S8)>

The fourth unit 34 in the information obtaining apparatus 3 forms the difference image using the pair of images for maximizing Expression 1. Specifically, a new image is generated by calculating a difference of the pixel values of the pixels corresponding to the first image and the second image subjected to the position adjustment. More specifically, when it is assumed that a certain pixel in the first image has a pixel value S(x, y), and a pixel in the second image corresponding to the certain pixel has a pixel value P(x, y), the new image has a pixel value proportional to (S−k·P). Here, (x, y) represents a coordinate position of the image. Further, the coordinate position is a coordinate position subjected to the position adjustment. The coefficient k is the same coefficient which maximizes Expression 1 in step S7.

A method for generating a finally processed image includes a method for generating an image by selecting and processing single images from a plurality of the obtained image data pieces. In addition to the above-described one, a processed image is separately generated by performing the averaging processing and the like on other images having close imaging conditions to that of the selected single image, and a final image can be generated by calculating the processed images. The close imaging conditions include, for example, a close imaging time and a close imaging wavelength.

Further, a processed image group can be generated by performing noise removal processing, averaging of images, and the like on a plurality of the captured image data pieces in advance. It is desirable that a plurality of images is selected from the processed image group and set as the above-described first image and second image, and a final difference image is generated from these images and the coefficient k to extract the blood vessel image therefrom.

The information about the blood vessel as an output of the present apparatus is not limited to the image data including the blood vessel part and may be a result extracting certain information from the image data. For example, the information about the blood vessel may be graphed data of distribution of pixel values on a line segment including the blood vessel part in the image data. The information about the blood vessel may be a value itself of the index value, the blood vessel image intensity, or the like.

The output from the present apparatus may be a detection result of presence or absence of specific data and data having a specific characteristic. For example, an image of a certain region, such as a joint is captured, an average of pixel values of the region including the joint is calculated for each joint, and the average can be compared to that of another joint. Further, presence of a specific region which is suspected of a disease, an injury, and the like because the average value of the pixel values is especially low or high compared to the other joint can be detected from the imaged data. As an output from the apparatus when the specific region is detected, processing can be performed for displaying a message informing the detection of the specific region and a determination result. Such processing directly processes and calculates the imaged data without performing imaging processing on the imaged data, so that an arithmetic operation can be performed at high speed.

Figure 7:
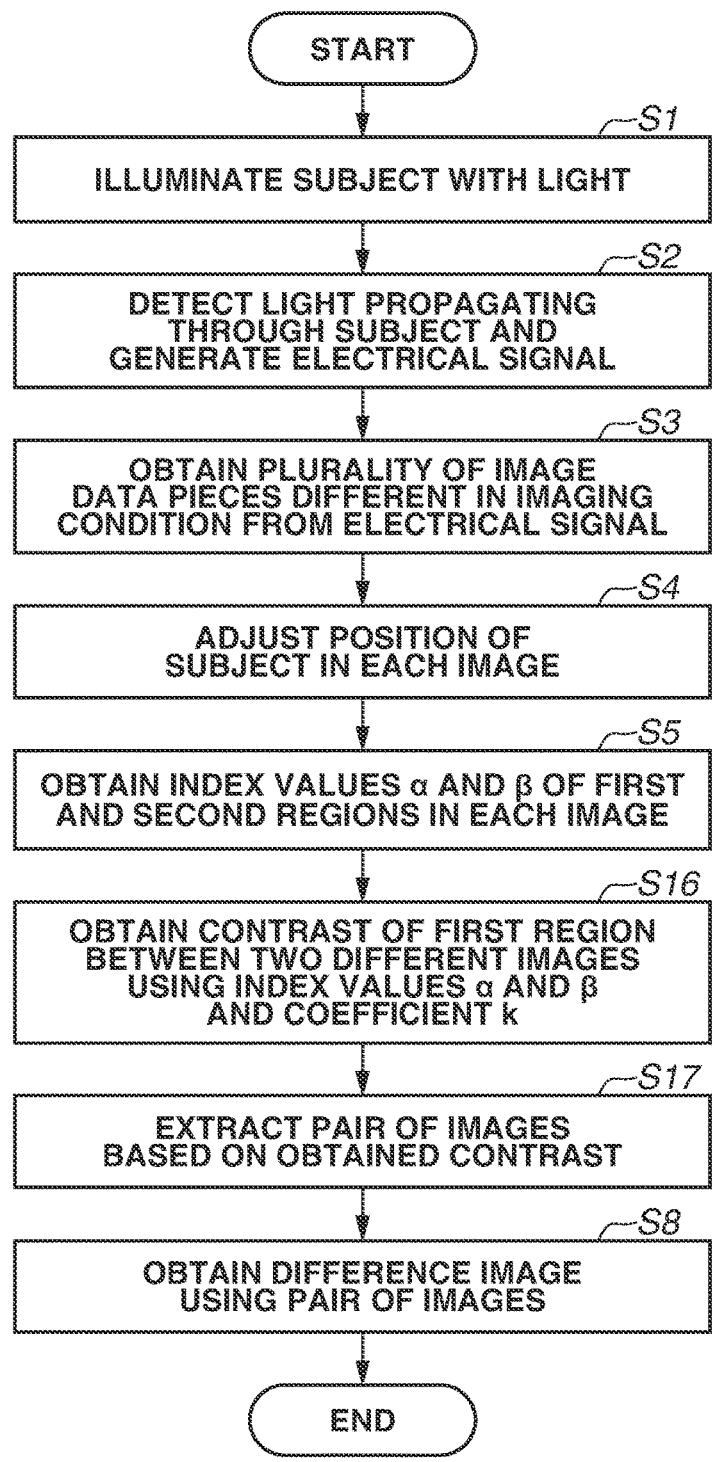
FIG. 7 is a flowchart illustrating an example of a method for obtaining information according to one or more aspects of the present disclosure.

According to the first exemplary embodiment, the blood vessel image intensity is evaluated as the selection method of the two images for generating the difference image, in contrast, according to a second exemplary embodiment, a contrast is evaluated for extracting two images. According to the present exemplary embodiment, a schematic diagram of an image capturing apparatus is similar to that in FIG. 1. FIG. 7 illustrates an image forming method according to the present exemplary embodiment. In FIG. 7, the same processes as those in FIG. 2 are denoted by the same reference numerals and their descriptions are omitted below.

The processes to step S5 are similar to those in the first exemplary embodiment. After step S5, in step S16, a contrast of the first region between the two different images is obtained using the index values α and β and the coefficient k. In step S17, the third unit 33 extracts a pair of images for maximizing the obtained content. Lastly, in step S8, the fourth unit 34 obtains a difference image using the pair of images.

With reference to FIG. 6, a contrast value of the blood vessel image in the difference image generated by the differential processing using the first image and the second image is expressed by the following Expression 2.

$$C3=|(\alpha1-k\cdot\alpha2)-(\beta1-k\cdot\beta2)|/|(\alpha1-k\cdot\alpha2)+(\beta1-k\cdot\beta2)| \quad \text{Expression 2}$$

Contrast values C are calculated in combinations of all of the pairs of images and the coefficient k, and the first image, the second image, and the coefficient are determined with which the contrast value C of the blood vessel image in the difference image is maximized. Further, it is desirable to generate a third image by subtracting k times the second image from the first image.

Regarding the evaluation of the contrast value, when the ROI is set, it is desirable to calculate the contrast value using differences of values of α1, α2, β1, and β2 with respect to the lowest pixel value in the ROI and perform processing based on the calculated contrast value. The value of the coefficient k may be simply set to one for increasing a processing speed or another value.

A search for the value of the coefficient k can be performed in a wide numerical range, however, when the value of the coefficient k is extremely large or small, a difference image to be generated is close to one of images actually used in the differential processing. In other words, it is highly likely that the contrast of the blood vessel image has a value not much different from a contrast of one of the original images. The present inventor found that when images different in imaging conditions of a human body, for example, images different in imaging time and blood flow are compared with each other, a variation in a pixel value of a certain region is typically within twice the pixel value. Thus, the search range of the coefficient k may be sufficient and desirable to be set to 0.5 or greater and 2.0 or less.

It is desirable to select the first image and the second image or the value of the coefficient k so that a pixel value does not have a negative value in all regions in an image generated by the differential processing. Further, when the ROI is set, it is desirable to select the first image and the second image or the value of the coefficient k so that a pixel value does not have a negative value in the ROI of the difference image as with the above case. Furthermore, when a lowest value of the pixel value in the ROI of the difference image has a negative value as a result of the selection of the images and the coefficient k for maximizing the contrast, it is desirable to add a value to all pixels so that the lowest pixel value in the ROI becomes zero. It is also desirable to generate an image by assigning a maximum value in the ROI to a maximum value of a brightness value. Accordingly, overexposure and underexposure can be suppressed in the ROI in the image.

Figure 8:
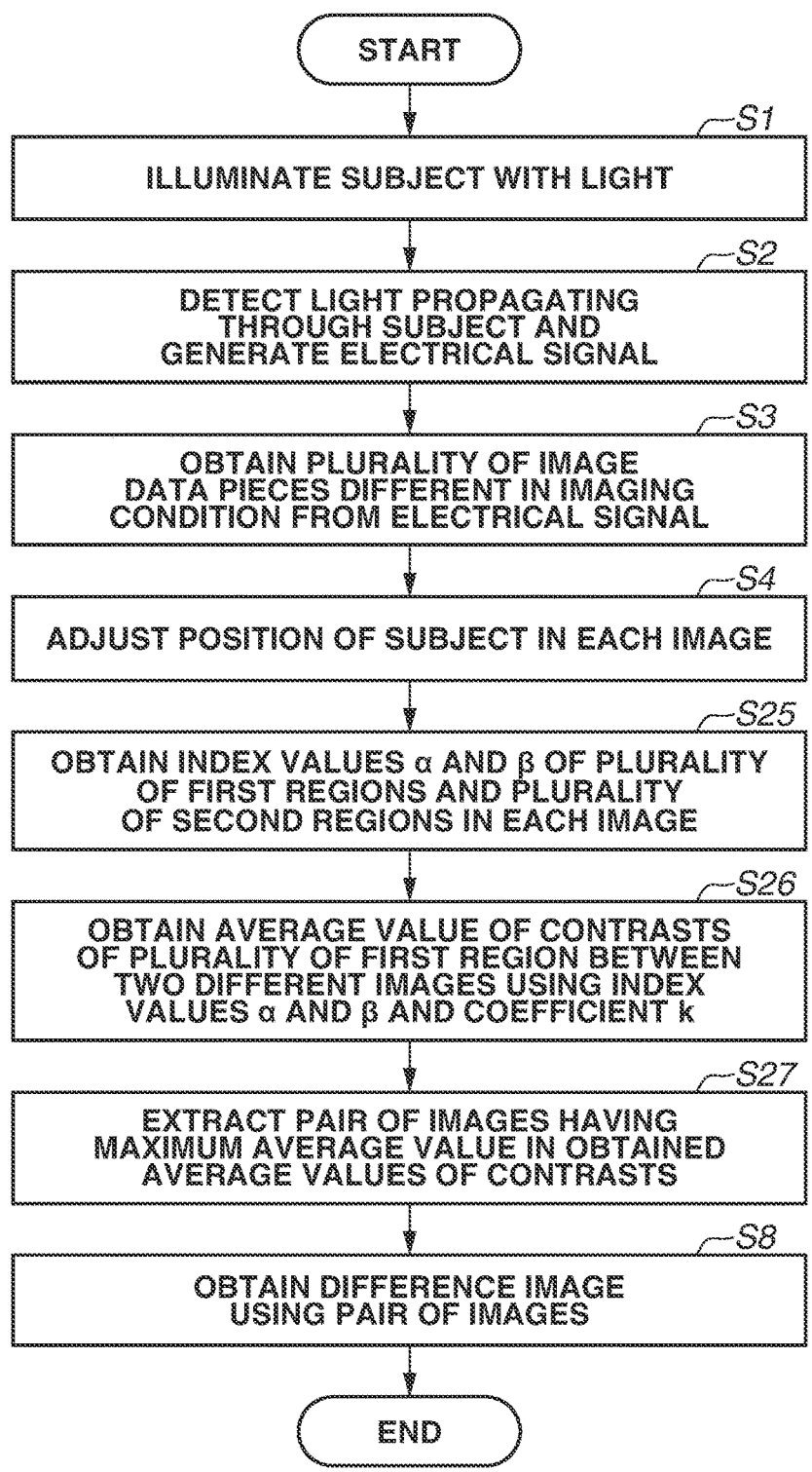
FIG. 8 is a flowchart illustrating an example of a method for obtaining information according to according to one or more aspects of the present disclosure.

According to the first and second exemplary embodiments, there are one each of the first region and the second region, however, according to a third exemplary embodiment, a case is described in which a plurality of first regions and second regions is selected. In other words, this is a case that a blood vessel image is extracted by capturing blood vessel images of a plurality of portions. The case includes when a wide region including a plurality of joints, such as an entire arm and an entire leg is imaged at the same time, and the blood vessel images of the vicinity of the plurality of the joints or images of a new blood vessel group are captured. According to the present exemplary embodiment, a schematic diagram of an image capturing apparatus is similar to that in FIG. 1. FIG. 8 illustrates an image forming method according to the present exemplary embodiment. In FIG. 8, the same processes as those in FIG. 7 are denoted by the same reference numerals and their descriptions are omitted below.

The processes to step S5 are similar to those in the second exemplary embodiment. After step S5, in step S26, a contrast value of each blood vessel image between two different images is obtained using the index values α and β and the coefficient k, and an average value of the contrast values is obtained. In step S27, the third unit extracts a pair of images for maximizing the average value of the obtained contrast values. Lastly, in step S8, the fourth unit 34 obtains a difference image using the pair of images. The contrast value can be expressed using Expression 2 described according to the second exemplary embodiment.

The selection of the first image and the second image and the setting of the coefficient k are not limited to a method for determining the average value of the contrasts of each blood vessel image as described above. For example, a variation in the contrast values of each blood vessel image can be evaluated using a standard deviation and other values so that any of the contrast values of each blood vessel image is not extremely lowered. For example, a target contrast value is set in advance, a variation in the contrast of each blood vessel image from the target value is expressed by the standard deviation, and the first image, the second image, and the coefficient k can be set so as to minimize the standard deviation. Further, it is desirable to set an evaluation function with respect to the contrast values of a plurality of the blood vessel images and select images and the coefficient for minimizing the evaluation function value.

Further, in step S27, instead of selecting two images for maximizing the average value of the contrast of each blood vessel image in the difference image, two images may be arbitrarily selected from pairs of images of which the average value of the constants of each blood vessel image in the difference image is a desired value or larger.

Further, as with the first exemplary embodiment, the blood vessel image intensity can be evaluated instead of the contrast value. Furthermore, it is desirable to select a pair of images so that an average value of the blood vessel image intensity of the difference image in each region becomes the highest and perform the differential processing since an image can be generated in which all blood vessels in a plurality of regions are easy to be viewed. In this regard, when the average value of the blood vessel image intensity in each region is calculated, the average value can be calculated by weighting the blood vessel image intensity for each region. For example, it is desirable to put a heavier weight on the blood vessel image intensity of the region of which the blood vessel image is required to be the easiest to be viewed.

Figure 9:
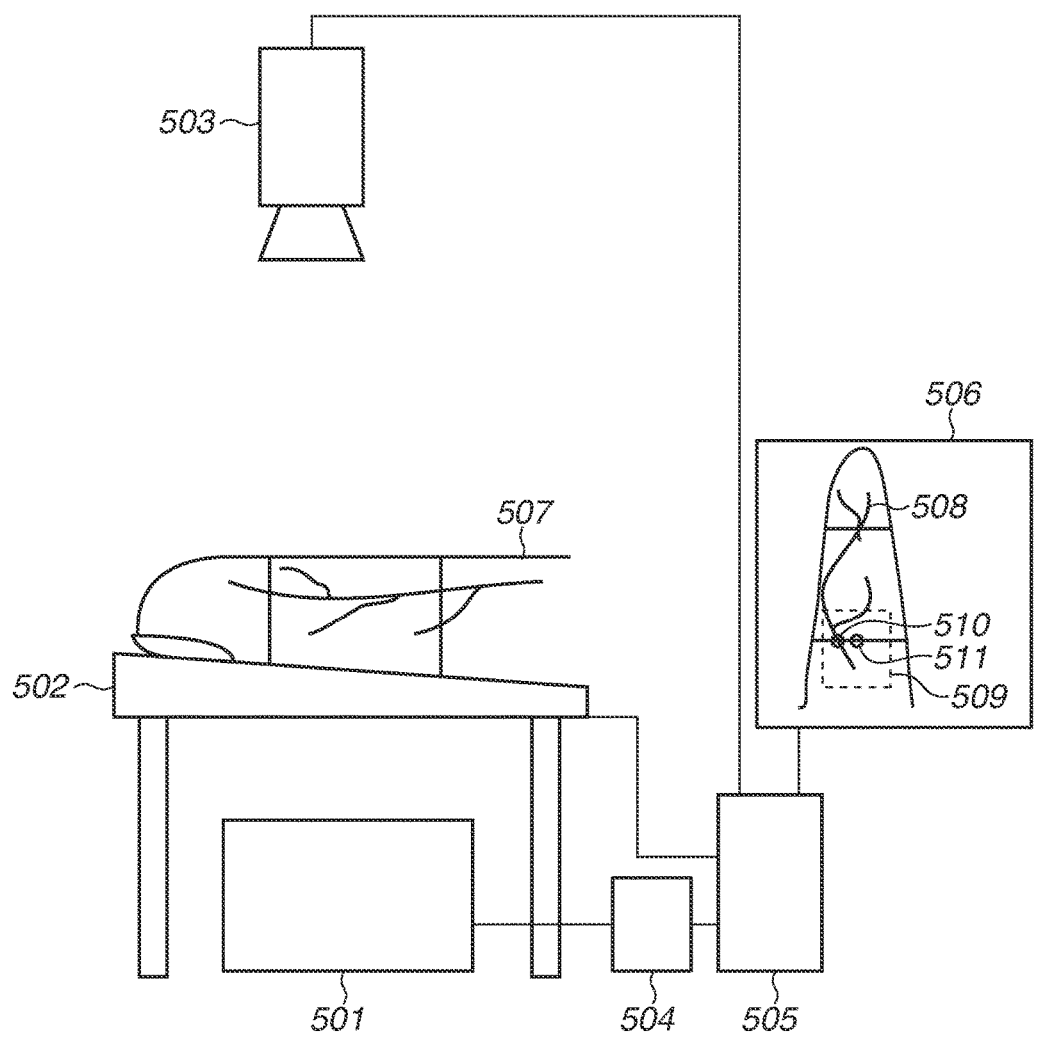
FIG. 9 is a schematic diagram illustrating an image capturing apparatus according to according to one or more aspects of the present disclosure.

An image capturing apparatus according to a fourth exemplary embodiment is described below with reference to FIG. 9. FIG. 9 is a schematic drawing illustrating the image capturing apparatus according to the present exemplary embodiment. The image capturing apparatus includes a light source 501, a retainer 502, an imaging camera 503, a light source driving power source 504, a control processing personal computer (PC) 505, and a monitor 506. An object as an imaging target is a finger 507. A tourniquet is applied to an upper arm, which is not illustrated, between the finger 507 and a heart, and an applied pressure is controlled by a signal from the control processing PC 505.

The light source 501 emits light of wavelength 760 nm to the finger 507, and the imaging camera 503 detects the light transmitted through the hand and generates an image signal based on the detected light. The light source 501 includes LEDs emitting the light of wavelength 760 nm arranged in an array. The imaging camera 503 is a camera having a sensitivity to the light of wavelength 760 nm and outputs a digital signal. Further, the imaging camera captures a moving image of 5 frames per second for 40 seconds and obtains each frame as image data.

A pressure applied to the tourniquet at the start of imaging is 0 mmHg. Next, when 10 seconds has elapsed from immediately after the start of imaging, the pressure is applied to the tourniquet to 140 mmHg. Subsequently, when 10 seconds has elapsed after applying the pressure, the applied pressure is returned to 0 mmHg for 5 seconds. Subsequently, the imaging is further performed for 10 seconds and then terminated. The control processing PC 505 controls the pressure applied to the tourniquet.

The control processing PC 505 obtains the image signal generated by the imaging camera 503. The control processing PC 505 generates image data based on the obtained image signal and displays a generated moving image or an image of each frame on the monitor 506. Accordingly, an operator can confirm an imaging result of the blood vessel in the target joint as the imaging target of the finger 507 displayed on the monitor 506.

The control processing PC 505 performs a position adjustment arithmetic operation on the blood vessel image in each captured frame by performing pattern matching on the blood vessel part of images of a second and subsequent frames with respect to the blood vessel image of a first frame. Accordingly, a positional deviation of the blood vessel image due to a movement of a subject person's hand during the imaging is corrected in the image of each frame, and an image is obtained in which the blood vessel image is recorded at the same position.

Further, the control processing PC 505 evaluates and stores an intensity of the captured blood vessel 508. First, the operator sets a ROI 509 in an image already subjected to the position adjustment, specifies a pixel 510 on a blood vessel in the ROI 509 as a first region, and specifies a pixel 511 of a fat part in the vicinity as a second region.

Next, the control processing PC 505 reads and stores values of the pixels 510 and 511 in each frame. Further, the control processing PC 505 extracts and stores a lowest pixel value in the ROI 509. The control processing PC 505 selects a pair of frames of which a value obtained by subtracting a change amount of the value of the pixel 511 from a change amount of the value of the pixel 510 is the maximum from the images already subjected to the position adjustment. Subsequently, the control processing PC 505 generates a difference image of these frames and displays the difference image on the monitor 506. At the same time, the control processing PC 505 calculates a contrast of the target portion from a minimum value in the ROI.

The control processing PC 505 controls a light amount of the light source 501 using the light source driving power source 504. Further, the control processing PC 505 appropriately adjusts various imaging conditions, such as the sensitivity and an exposure time of the imaging camera 503. According to these operations, the blood vessel in the target joint can be imaged in high contrast.

When an image supposed to be the new blood vessel group is found in the ROI other than the artery or the vein, analysis processing is further continued.

The operator or the control processing PC 505 specifies a pixel in the new blood vessel group (not illustrated) as the first region and specifies a pixel which is out of the new blood vessel group and not in the artery nor the vein (not illustrated) as the second region. The pixel value of the first region and the pixel value of the second region in each frame are extracted. Subsequently, the difference image is generated by the procedure similar to the above-described one, and the new blood vessel group is extracted with high accuracy.

By using the image capturing apparatus according to the present exemplary embodiment, an image from which a blood vessel image is extracted can be obtained.

Figure 10:
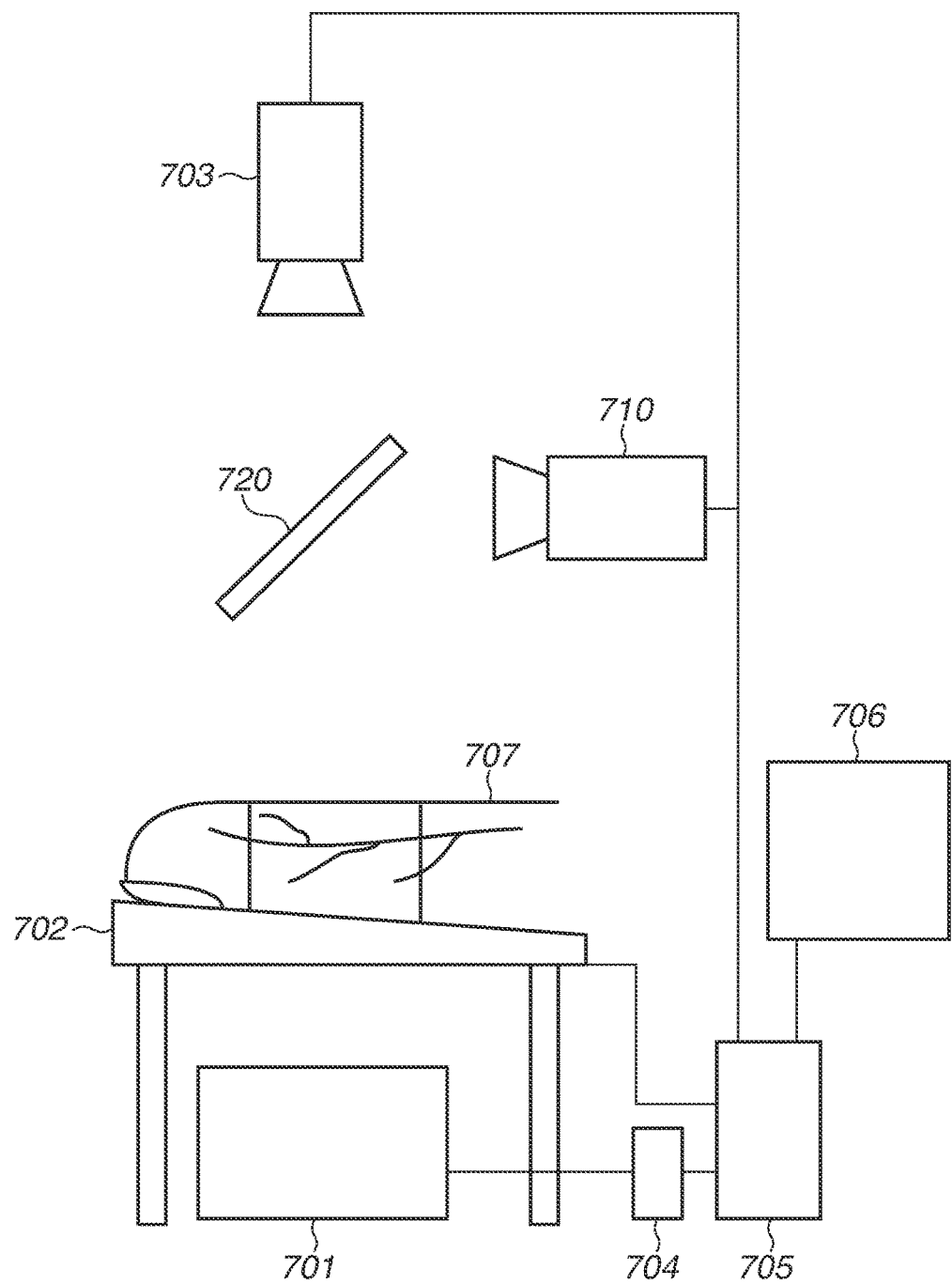
FIG. 10 is a schematic diagram illustrating an image capturing apparatus according to according to one or more aspects of the present disclosure.

An image capturing apparatus according to a fifth exemplary embodiment is described below with reference to FIG. 10. FIG. 10 is a schematic drawing illustrating the image capturing apparatus according to the present exemplary embodiment. The image capturing apparatus includes a light source 701, a retainer 702, an optical path splitting element 720, imaging cameras 703 and 710, a light source driving power source 704, a control processing PC 705, and a monitor 706. An imaging target is a finger 707.

The light source 701 simultaneously emits light of wavelength 760 nm and light of wavelength 940 nm to the finger 707, and the imaging cameras 703 and 710 detect the light transmitted through the hand (transmitted light). The imaging cameras 703 and 710 generate image signals based on the detected light. The light source 701 includes LEDs emitting the light of wavelength 760 nm and LEDs emitting the light of wavelength 940 nm arranged alternately. An optical path splitting element 720 is a dichroic mirror which reflects the light of wavelength 940 nm and transmits and the light of wavelength 760 nm.

The imaging cameras 703 and 710 respectively have sensitivities to the light of wavelength 760 nm and the light of wavelength 940 nm. Further, the imaging cameras 703 and 710 perform imaging at the same time and store image data pieces obtained by the respective cameras in the control processing PC 705.

The control processing PC 705 performs position adjustment of blood vessel images on images captured by the respective cameras. Accordingly, a positional deviation of the blood vessel image due to an arrangement error of the optical system is suppressed in each image. The control processing PC 705 generates images by performing the position adjustment of the blood vessel image on all the images obtained by the imaging cameras 703 and 710.

The control processing PC 705 extracts a pair of images from these images, generates a difference image, and displays the difference image on the monitor 706 in a similar way to the fourth exemplary embodiment.

The control processing PC 705 controls a light amount of the light source 701 using the light source driving power source 704. Further, the control processing PC 705 appropriately adjusts various imaging conditions, such as the sensitivities and exposure times of the imaging cameras 703 and 710. According to these operations, the blood vessel in the target joint can be imaged in high contrast.

By using the image capturing apparatus according to the present exemplary embodiment, a blood vessel can be imaged by different wavelengths, and a blood vessel image can be extracted by the differential processing thereon.

Figure 11:
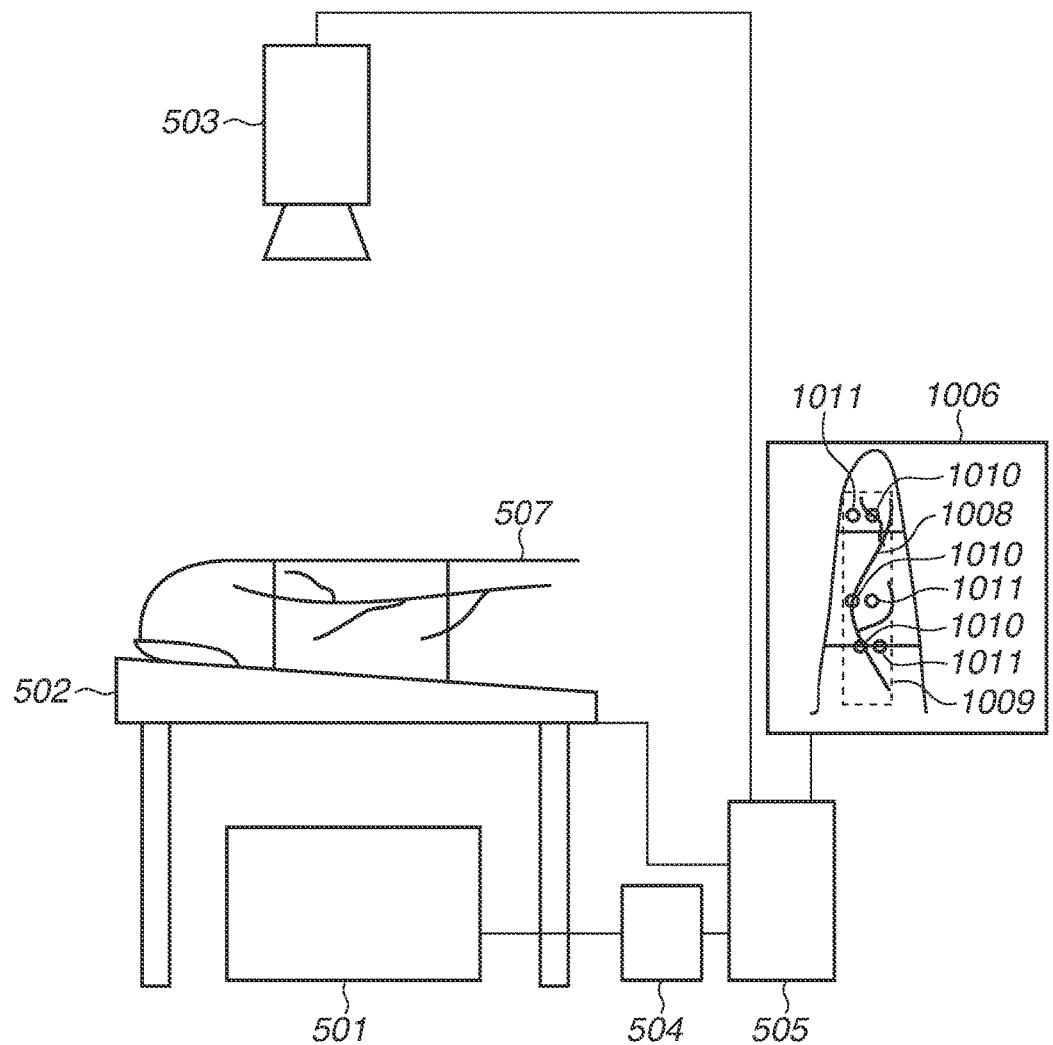
FIG. 11 is a schematic diagram illustrating an image capturing apparatus according to according to one or more aspects of the present disclosure.

According to a sixth exemplary embodiment, an example of an image capturing apparatus is described in which a wide region of interest (ROI) 1009 including a plurality of joints is set as illustrated in FIG. 11, and pixel values of blood vessels 1010 and pixel values of fat parts 1011 at a plurality of positions in the ROI are evaluated. However, only differences from the fourth exemplary embodiment are described.

According to the present exemplary embodiment, blood vessel image contrast values at a plurality of points are calculated from the blood vessel parts (the first regions) 1010 and the fat parts (the second regions) 1011 at the plurality of the positions. Two images are selected from 200 captured images and subjected to the differential processing by multiplying the coefficient k, and an image is generated from which a blood vessel image is extracted. Each of the two selected images is selected again from the captured images, and further the difference images are sequentially generated from the respective pairs of images by changing the value of the coefficient k from 0.5 to 2.0. Further, contrast values of the blood vessel images at a plurality of points are calculated with respect to the generated difference images. The contrast of each blood vessel image is calculated according to Expression 2. Further, a pair of images and the value of the coefficient k which maximize the average value of the blood vessel image contrast are determined and the difference image is generated.

By using the image capturing apparatus according to the present exemplary embodiment, a blood vessel can be extracted with high accuracy in a wide region of interest including a plurality of joints.

According to an information obtaining apparatus of the present disclosure, information about a blood vessel can be obtained with high accuracy.

While the present disclosure has been described with reference to exemplary embodiments, the scope of the following claims are to be accorded the broadest interpretation so as to encompass all such modifications and equivalent structures and functions.

This application claims the benefit of Japanese Patent Application No. 2015-242005, filed Dec. 11, 2015, which is hereby incorporated by reference herein in its entirety.

What is claimed is:

1. An information obtaining apparatus comprising:
   a first unit configured to obtain three or more image data pieces different in imaging conditions;
   a second unit configured to obtain a first index value of a first region which is at least a part of a region corresponding to an artery, a vein, or a new blood vessel group and a second index value of a second region which is at least a part of a region other than the region corresponding to the artery, the vein, or the new blood vessel group in the image data;

a third unit configured to select a pair of the image data pieces from the three or more image data pieces using the first index value and the second index value of the image data; and a fourth unit configured to obtain information about a blood vessel using the selected pair of the image data pieces, wherein, in a case where the first index value of a first image data in the three or more image data pieces is $\alpha 1$, the first index value of a second image data different from the first image data in the three or more image data pieces is $\alpha 2$, the second index value of the first image data is $\beta 1$, the second index value of the second image data is $\beta 2$, and k is a positive constant, the third unit selects the first image data and the second image data which maximize a value of a following expression as the pair of the image data pieces, $$|(\alpha 1 - k \cdot \alpha 2) - (\beta 1 - k \cdot \beta 2)|.$$

2. An information obtaining apparatus comprising:

a first unit configured to obtain three or more image data pieces different in imaging conditions;

a second unit configured to obtain a first index value of a first region which is at least a part of a region corresponding to an artery, a vein, or a new blood vessel group and a second index value of a second region which is at least a part of a region other than the region corresponding to the artery, the vein, or the new blood vessel group in the image data;

a third unit configured to select a pair of the image data pieces from the three or more image data pieces using the first index value and the second index value of the image data; and a fourth unit configured to obtain information about a blood vessel using the selected pair of the image data pieces, wherein, in a case where the first index value of a first image data in the three or more image data pieces is $\alpha 1$, the first index value of a second image data different from the first image data in the three or more image data pieces is $\alpha 2$, the second index value of the first image data is $\beta 1$, the second index value of the second image data is $\beta 2$, and k is a positive constant, the third unit selects the first image data and the second image data which maximize a value of a following expression as the pair of the image data pieces, $$|(\alpha 1 - k \cdot \alpha 2) - (\beta 1 - k \cdot \beta 2)|/|(\alpha 1 - k \cdot \alpha 2) + (\beta 1 - k\ \beta 2)|.$$

3. The information obtaining apparatus according to claim 1, wherein a single image data includes a plurality of the first regions and a plurality of the second regions, and each of the plurality of the first regions make a pair with the plurality of the second regions, and wherein, in a case where the first index value of one of the plurality of the first regions of a first image data in the three or more image data pieces is $\alpha 1$, the first index value of one of the plurality of the first regions of a second image data different from the first image data in the three or more image data pieces is $\alpha 2$, the second index value of one of the plurality of the second regions of the first image data is $\beta 1$, the second index value of one of the plurality of the second regions of the second image data is $\beta 2$, and k is a positive constant, the third unit obtains a value of a following expression for each pair of the first region and the second region and selects the first image data and the second image data which maximize an average value of obtained values of the following expression of each pair as the pair of the image data pieces, $$|(\alpha 1 - k \cdot \alpha 2) - (\beta 1 - k \cdot \beta 2)|/|(\alpha 1 - k \cdot \alpha 2) + (\beta 1 - k \cdot \beta 2)|.$$

4. The information obtaining apparatus according to claim 3, wherein the third unit obtains a value of a following expression for each pair of the first region and the second region and selects the first image data and the second image data which maximize an average value of obtained values of the expression of each pair as the pair of the image data pieces, $$|(\alpha 1 - k \cdot \alpha 2) - (\beta 1 - k \cdot \beta 2)|.$$

5. The information obtaining apparatus according to claim 1, wherein the fourth unit performs averaging processing on each of the pair of the image data pieces together with image data having a close imaging condition to the each of the pair of the image data pieces to generate two image data pieces and obtains the information about the blood vessel using the two image data pieces generated by performing the averaging processing.

6. The information obtaining apparatus according to claim 1, wherein the first index value or the second index value is a pixel value when the first region or the second region is constituted of a single pixel and is an average value, a maximum value, or a minimum value of pixel values of a plurality of pixels when the first region or the second region is constituted of a plurality of pixels.

7. The information obtaining apparatus according to claim 1, wherein the first region is at least a part of a region corresponding to an artery, a vein, or a new blood vessel group of a joint portion of a finger.

8. The information obtaining apparatus according to claim 1, wherein the second region is set near the at least the part of the region corresponding to the artery, the vein, or the new blood vessel group set as the first region.

9. The information obtaining apparatus according to claim 1, wherein each of the three or more image data pieces obtained by the first unit is image data of which a blood vessel part is subjected to position adjustment with each image data.

10. The information obtaining apparatus according to claim 1, wherein each of the three or more image data pieces obtained by the first unit is image data generated by performing averaging processing on image data pieces having a close imaging condition.

11. The information obtaining apparatus according to claim 1, wherein a different imaging condition includes a difference of a blood flow in an imaging portion.

12. The information obtaining apparatus according to claim 1, wherein a different imaging condition includes a difference of a wavelength of light illuminating an imaging portion.

13. The information obtaining apparatus according to claim 1, wherein the information about the blood vessel is generated as image data.

14. An image capturing apparatus comprising:

a light source configured to illuminate a subject including a blood vessel with light;

a detection unit configured to detect light emitted from the light source and propagating through the subject and generate an electrical signal; and an information obtaining apparatus configured to obtain information about the blood vessel using the signal from the detection unit, wherein the information obtaining apparatus is the information obtaining apparatus according to claim 1.

15. The information obtaining apparatus according to claim 2, wherein the fourth unit performs averaging processing on each of the pair of the image data pieces together with image data having a close imaging condition to the each of the pair of the image data pieces to generate two image data pieces and obtains the information about the blood vessel using the two image data pieces generated by performing the averaging processing.

16. The information obtaining apparatus according to claim 2, wherein the first index value or the second index value is a pixel value when the first region or the second region is constituted of a single pixel and is an average value, a maximum value, or a minimum value of pixel values of a plurality of pixels when the first region or the second region is constituted of a plurality of pixels.

17. The information obtaining apparatus according to claim 2, wherein the first region is at least a part of a region corresponding to an artery, a vein, or a new blood vessel group of a joint portion of a finger.

18. The information obtaining apparatus according to claim 2, wherein the second region is set near the at least the part of the region corresponding to the artery, the vein, or the new blood vessel group set as the first region.

19. The information obtaining apparatus according to claim 2, wherein each of the three or more image data pieces obtained by the first unit is image data of which a blood vessel part is subjected to position adjustment with each image data.

20. The information obtaining apparatus according to claim 2, wherein each of the three or more image data pieces obtained by the first unit is image data generated by performing averaging processing on image data pieces having a close imaging condition.

21. The information obtaining apparatus according to claim 2, wherein a different imaging condition includes a difference of a blood flow in an imaging portion.

22. The information obtaining apparatus according to claim 2, wherein a different imaging condition includes a difference of a wavelength of light illuminating an imaging portion.

23. The information obtaining apparatus according to claim 2, wherein the information about the blood vessel is generated as image data.

24. An image capturing apparatus comprising:
a light source configured to illuminate a subject including a blood vessel with light;
a detection unit configured to detect light emitted from the light source and propagating through the subject and generate an electrical signal; and
an information obtaining apparatus configured to obtain information about the blood vessel using the signal from the detection unit,
wherein the information obtaining apparatus is the information obtaining apparatus according to claim 2.

* * * * *